United States Patent [19]

Barger et al.

[11] 4,108,109

[45] Aug. 22, 1978

[54] BLOOD FILMING APPARATUS

[75] Inventors: J. P. Barger, Winchester; Joseph A. Holroyd, Nabnasset, both of Mass.

[73] Assignee: Dynatech Corporation, Burlington, Mass.

[21] Appl. No.: 469,099

[22] Filed: May 13, 1974

[51] Int. Cl.² .......................... B05C 13/02
[52] U.S. Cl. .......................... 118/52; 427/240
[58] Field of Search ................. 118/52–56; 117/101; 427/2, 240

[56] References Cited

U.S. PATENT DOCUMENTS

| 755,349 | 3/1904 | Bornman | 118/54 |
|---|---|---|---|
| 1,140,068 | 5/1915 | Roberts | 118/54 |
| 1,245,407 | 11/1917 | Ulrich | 118/54 |
| 3,280,792 | 10/1966 | Heyde | 118/52 |
| 3,467,059 | 9/1969 | Korner et al. | 118/53 |
| 3,577,267 | 5/1971 | Preston, Jr. et al. | 118/52 X |
| 3,705,048 | 12/1972 | Staunton | 118/52 X |
| 3,870,014 | 3/1975 | Buck | 118/501 X |

FOREIGN PATENT DOCUMENTS 449,741   7/1936   United Kingdom ............ 118/52

*Primary Examiner*—Mervin Stein
*Attorney, Agent, or Firm*—Cesari and McKenna

[57] ABSTRACT

Apparatus for forming a film of blood or other body fluid sample on a microscope slide. The slide is surrounded by a member adapted to catch and immobilize excess blood thrown from the slide by centrifugal force. The member, which advantageously rotates with the slide while positioned in a waste-receiving mode, advantageously comprises a pocket filled with highly porous blood-receiving material and is adapted to be moved vertically out of the waste-receiving mode to facilitate positioning and removal of the slide from the apparatus.

17 Claims, 10 Drawing Figures

BLOOD FILMING APPARATUS

BACKGROUND OF THE INVENTION

This invention relates to a an apparatus useful therein, for distributing blood on, say, a glass slide for subsequent inspection with a microscope. Such distribution if often referred to as "filming" by those working in medical laboratories.

There are a number of problems associated with the distribution of a blood sample on a glass slide. Perhaps the most obvious problem is that of obtaining an even distribution over the entire slide. The usual manual method consists of placing a drop of blood on the slide and then using a second slide to smear the blood along the slide. This technique usually results in poor lateral distribution, and the excessively narrow smear along the slide usually consists of excessively thick and ultrathin areas. To avoid such problems, centrifugal equipment was introduced which utilized centrifugal force to spread blood along the length of a spinning slide and utilized the acceleration of the slide to achieve a lateral distribution of the blood.

This centrifugal procedure is a substantial advance in filming, but it has at least two problems associated therewith: one of these relates to formation of aerosols and their distribution by air currents inherent in fast-rotating centrifugal devices. Clinical experience suggests that diseased samples may be a source of disease-bearing contaminants when processed in such devices unless adequate protective measures are taken. Another problem relates to excess blood being thrown off from the slide and collecting within the rotor enclosure. The problem is not only aesthetic in nature, but also involves additional cleaning and maintenance requirements and an undesirable threat of contamination of samples, and of equipment from samples, during handling. Such equipment contamination can also affect operation of the mechanisms of the centrifugal device.

SUMMARY OF THE INVENTION

It is a principal object of the present invention to provide novel centrifugal apparatus especially useful in distributing, i.e., filming, liquid physiological specimens over surfaces, e.g., glass slides.

Another object of the invention is to provide improved processes for safe filming of such samples, especially blood samples.

A further object of the invention is to provide apparatus which comprises waste-receiving means capable of eliminating or minimizing dispersion of pathogenic material into the laboratory air.

Another object of the invention is to provide apparatus wherein the waste-receiving means intercepts, immobilizes and holds excess sample, thereby protecting the internal surfaces of the apparatus from contamination and reducing maintenance and cleaning.

Another object of the invention is to provide an improved mechanical means to move the waste-immobilizing means and glass slide-holding means relative to one another, thereby allowing operation without interfering with the manipulative procedures of the operator.

Other objects of the invention will be obvious to those skilled in the art, on their reading of the instant disclosure.

The above objects have been substantially achieved by the construction of apparatus comprising a waste-receiving member mounted about the slide surface which is to be subjected to spinning. The waste-receiving member is advantageously so mounted that it will spin with the slide, thereby eliminating any undesirable relative motion that could result in formation of blood aerosols between the slide and receiving member. However, even when such rotation of the waste-receiving member is provided, the receiving member and slide are mounted on independent support members which can be raised and lowered relative to one another to facilitate removal of the slide from the apparatus.

It has been found particularly advantageous to have this waste-receiving member supported on a mechanism which is actuated by a cover means which assures that the waste-receiving member will be placed automatically in the proper relation to the slide whenever the centrifuge is closed and ready for operation.

By "slide" is meant that member which provides a sample-receiving surface on which a physiological sample, such as blood, is to be filmed. Usually a glass slide of the type used by microscopists will be utilized. However, any member providing such a sample-receiving surface can be a functional equivalent to such a slide for the purposes of describing and claiming the instant invention.

A particular advantage of the invention described herein is the immediate enclosure of pathogenic material within the waste-receiving means as it leaves the surface of a spinning slide. Such immediate capture takes place before the pathogenic material, which may be diseased cells or the like, can become entrained in air currents and exhausted from the apparatus into the atmosphere of a laboratory as contaminants. The most advantageous distances between the edge of the slide, or other sample-bearing surfaces on which a film is to be spread and the waste-receiving means are about from 0 to 0.25 inches, although greater distances, say to 0.5 inches, are suitable in some circumstances and, at any distance at which the liquid droplets are substantially captured within the waste-receiving means, the apparatus of the invention is a marked improvement over the art.

To maintain this clearance in embodiments of the invention in which the waste-receiving means does not rotate, it is sometimes desirable to provide a sample-receiving means which is circular or polygonal in shape, i.e. is adapted to rotate without its periphery moving too far from the waste-receiving means.

The waste-receiving member can be any receptacle so mounted proximate to the periphery of the surface of the slide that it intercepts, immobilizes and holds the waste material centrifugally deposited thereon. Waste blood so immobilized can be disposed of without contact with hands of the operator. Most of the remaining discussion in this disclosure will relate to the particularly advantageous use of a porous medium in this intercepting and immobilizing application. Nevertheless, it should be realized that other mechanical devices can function as waste-receiving means. Other embodiments of waste-receiving means could be simple solid-bowl centrifuge-like devices without any blood restraining means, except a barrier to reverse flow of waste.

In typical work, such as the filming of blood samples prior to cytological inspection or counting, about 20 to 200 specimens can be run before replacing a porous waste-receiving means depending on various design parameters. It has been found that, if a portion or all of the liquid impermeable cover of the waste-receiving means is transparent, contamination can be monitored visually and the maximum usage can be achieved before replacement or cleaning.

Another advantageous embodiment of the invention, one particularly helpful in facilitating a safe disposal of the porous pads, is that wherein the porous pad is impregnated with a disinfectant which is activated by the excess liquid spun off from the physiological sample being coated for filmed on the sample display surface.

A porous waste blood-receiving pad described herein is advantageous because it provides a plurality of functions: after the centrifugal force has forced the immobilized waste material far back into the porous medium, the medium can act as a means to mechanically hold the material from flowing out before it is fully dried or immobilized on the surface area of the porous material. The porous medium also can serve to hold a disinfectant. From this it follows that the porous medium does not act primarily as a filter but as a means to receive the excess specimen within a relatively becalmed zone and to hold it in said zone. However, when a porous mass such as a filter medium is so used, it also acts as a means to filter whatever air does pass therethrough.

In one embodiment of the invention, accommodation is made for a plurality of slides mounted one above the other. In such a case, the waste-immobilizing means will be made deep enough so that it may receive waste spun off from all the slides.

ILLUSTRATIVE EMBODIMENT OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions are selected and included for purposes of illustration in order that others skilled in the art will more fully understand the invention and the principles thereof and will be able to modify it and embody it in a variety of forms, each as may be best suited in the condition of a particular case.

Figure 1:
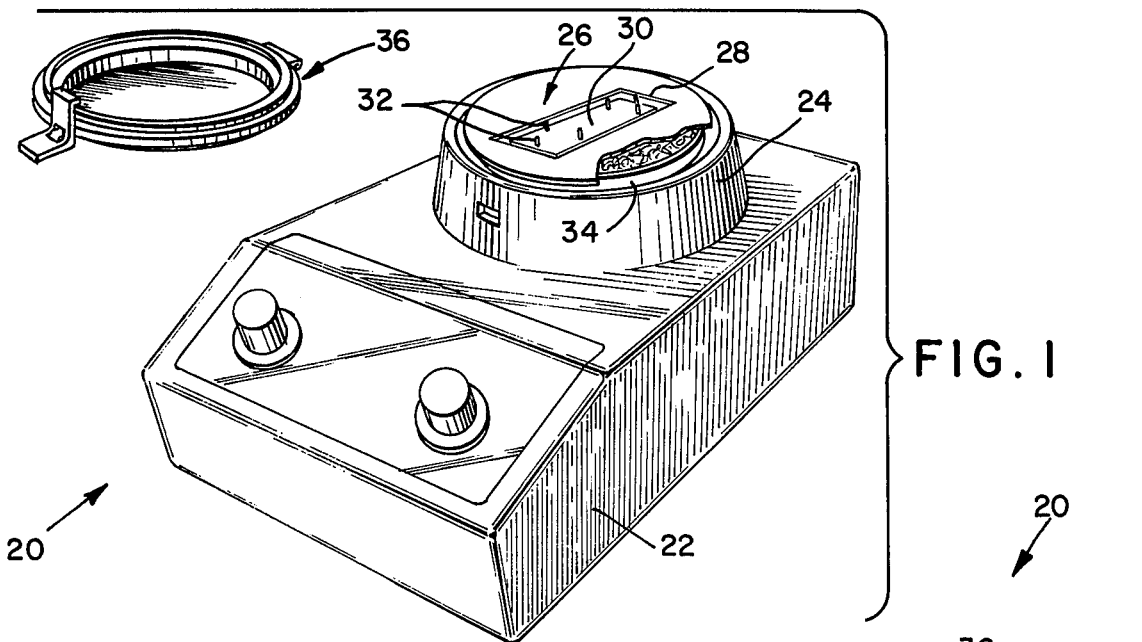
FIG. 1 is perspective view of the apparatus with its cover removed.

Referring to FIG. 1, it is seen that a specimen-filming apparatus 20 has a housing 22 comprising a turret section 24. A generally circular filter medium 26 is seen to surround an oblong area 28 cut into the filter medium 26. A slide supporting member 30 is adapted to hold a slide (portion shown at 31) within the aforesaid area 28. Member 30 has pins 32 projecting upwardly therefrom. These pins 32 are adapted to engage a slide member and keep it from being spun off member 30 during spinning motion imparted thereto during use of the apparatus. Filter medium 26 is supported on a filter support plate 34. A cover 36 is adapted to fit on turret section 24.

Figure 2:
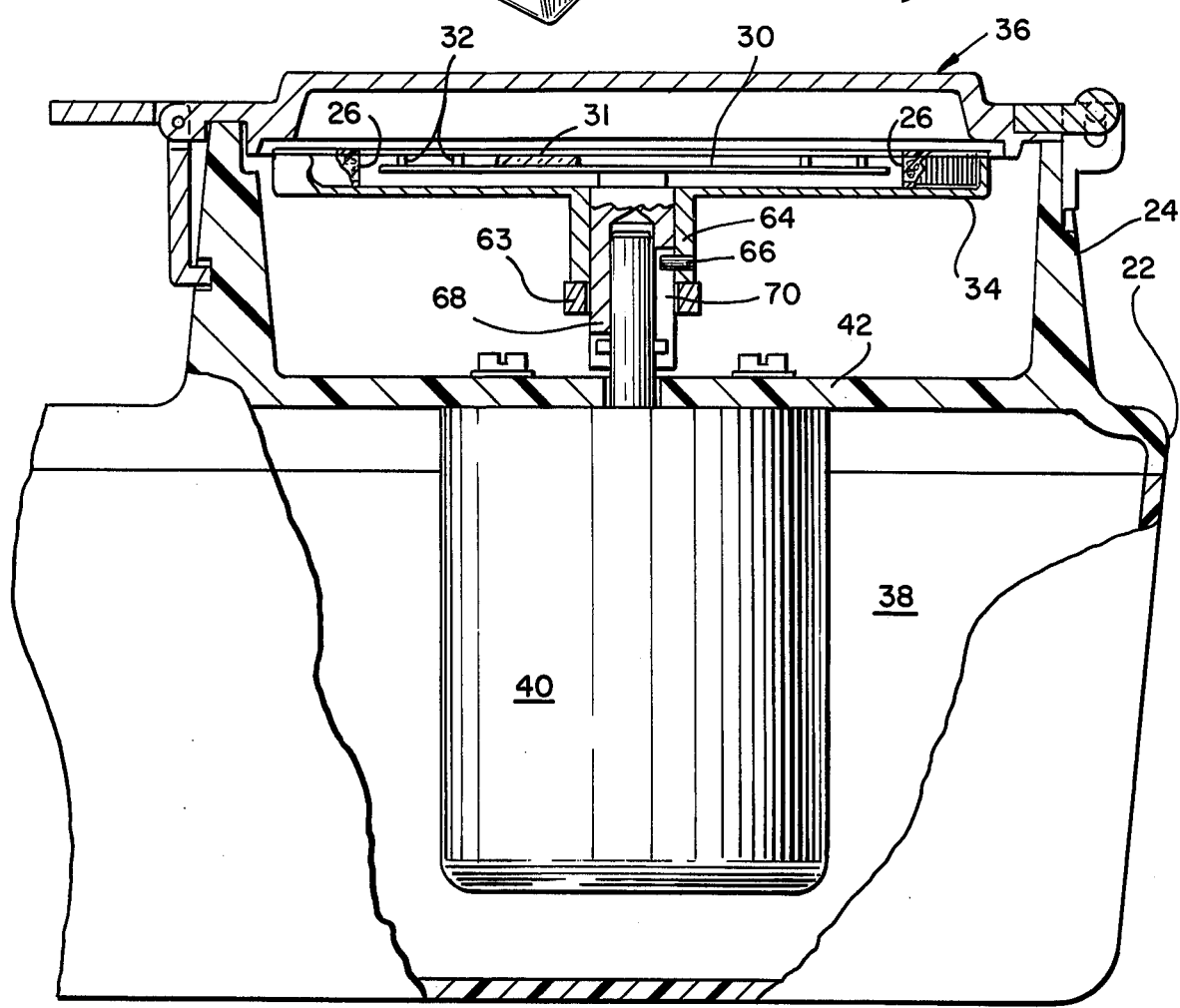
FIG. 2 is a section in elevation showing the apparatus of the invention.
Figure 3:
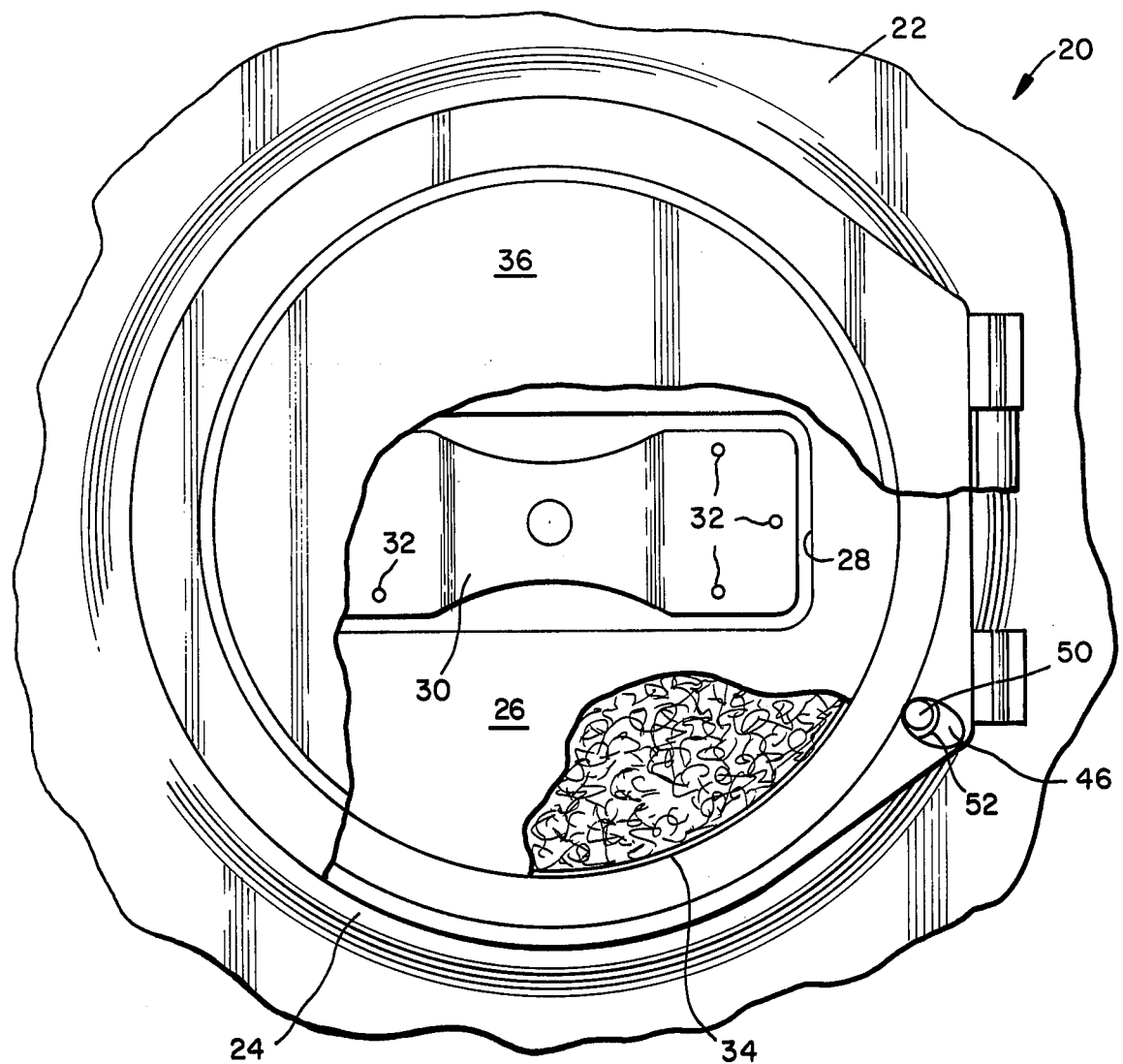
FIG. 3 is a plan view of the apparatus of FIG. 2.
Figure 4:
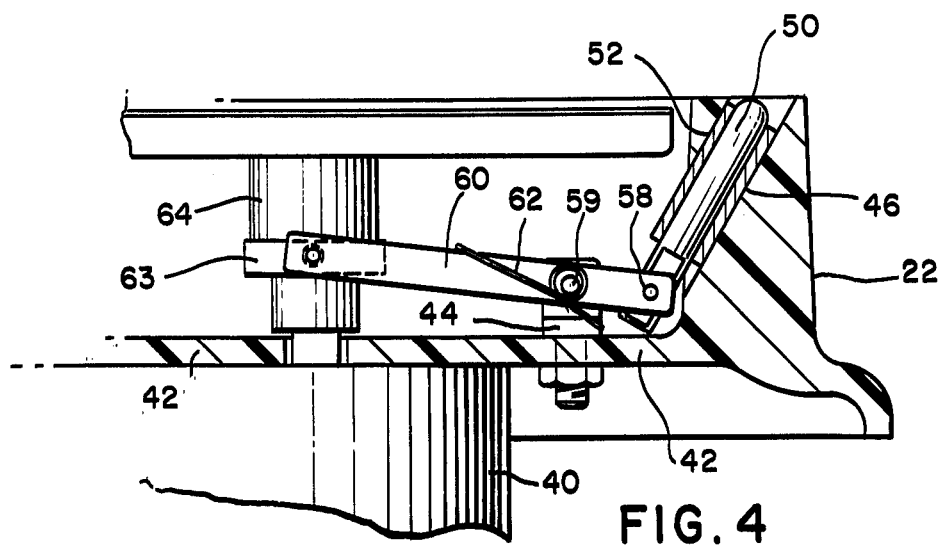
FIG. 4 is an elevation of a cover-actuated push rod assembly showing its selective lift action with respect to the apparatus of FIG. 2.

FIG. 2 illustrates how cover 36, turret section 24 and housing 22 cooperate to form a motor chamber 38. Motor 40 is attached to a motor bracket plate 42 which forms an integral molded part of turret section 24 and also carries a fulcrum post member 44 (best seen in FIG. 4). Post member 44 is securely bolted into plate 42. Turret section 24 has an aperture 46 leading upwardly and outwardly through one wall thereof (see FIG. 4). A push rod 50 is positioned for slidable movement within sleeve 52 in aperture 46.

Push rod 50 is pivotally attached by a pivot pin 58 to a lever arm 60 which is itself pivotally attached by a pivot pin 59 to fulcrum member 44 so that a thrust downwardly on push rod 50 will result in lowering one end of lever arm 60 and in a relatively greater raising of the other end of lever arm 60.

It will be appreciated that this pushing action on rod 50 can be and is, in the illustrated embodiment of the invention, achieved by lowering the cover 36.

Figure 5:
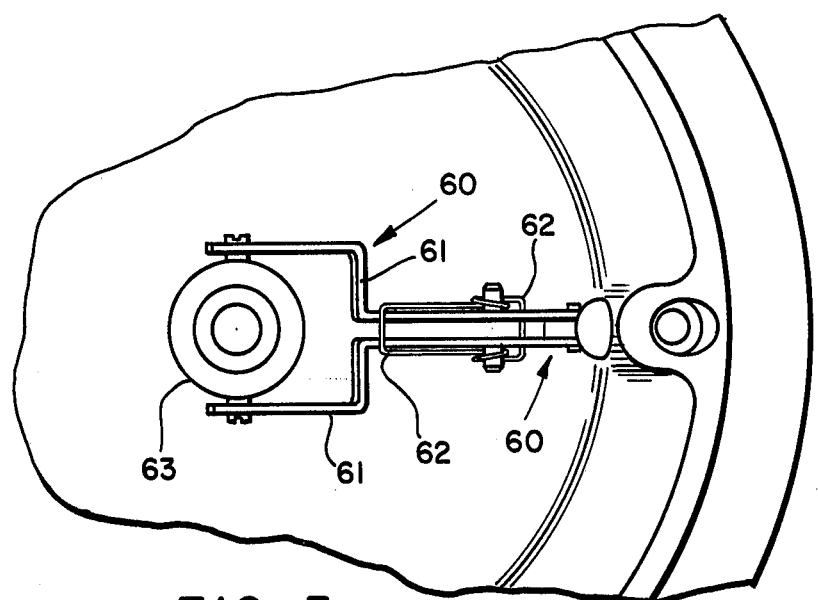
FIG. 5 is a plan view of the push rod assembly of FIG. 4.

As best seen in FIG. 5, lever arm 60 is formed of clevis member, and its movement is biased by spring means 62. The spring is conveniently constructed of 0.037-inch diameter music wire.

Each arm of the clevis is attached to a lift ring 63 which is adapted to lift and lower a rotor member 64. Rotor member 64 is integral with — that is adapted to rotate with — the filter support plate 34. Filter support plate 34 is, therefore, subjected to being raised by the action of the clevis pin on lift ring 63 in response to the opening and shutting action of the cover. This allows the cover member to act as a primary actuating lever for raising and lowering the filter pad in relation to the slide-supporting member 30. The amount of lift is that which will allow an operator's fingers to pick up the slide conveniently without touching the filter pad. This will usually be about 0.5 inch.

It should be recognized that, although the vertical or lift movement between rotor member 64 and slide support member 30 must be independent, the rotational movement of each of members 64 and 30 is at the same number of revolutions per minute (spin) and depends on a locking means such as locking pin 66 which fits into central motor shaft sleeve 68. This pin 66 moves in a vertical slot 70 so that it does not interfere with the vertical movement of the rotor.

Figure 6:
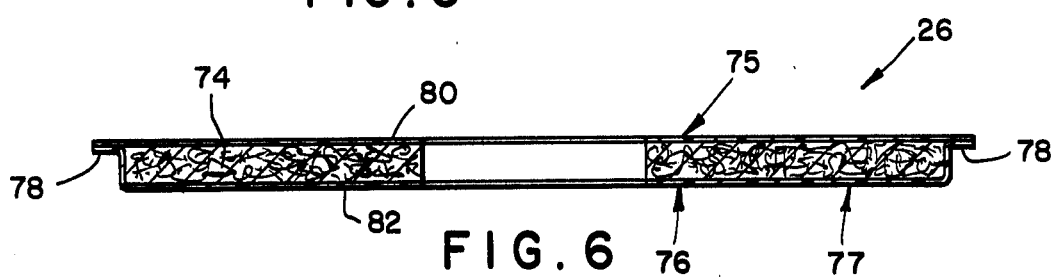
FIG. 6 is a section of a porous element used in the invention.
Figure 7:
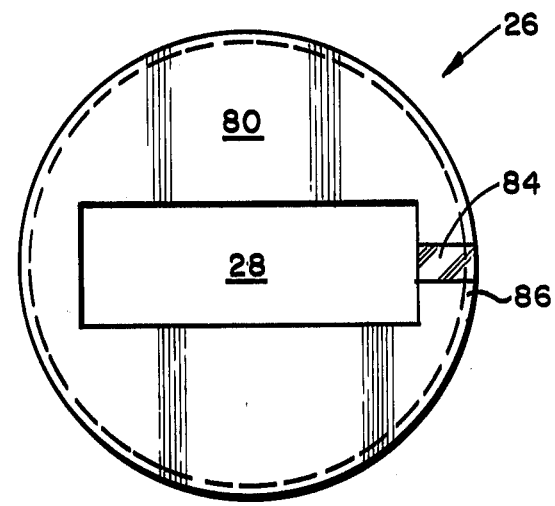
FIG. 7 is a plan view of the element of FIG. 6.

The filter means 26 illustrated in FIGS. 6 and 7 is a porous filter medium 74, e.g. an open celled polyurethane foam. This filter material has a pore size large enough to allow blood flow to the periphery under centifugal force and small enough so that blood will not flow back when the rotor is at rest. The filter medium is packaged in an outer, liquid-impermeable casing 77 which is formed of a thin film of plastic material, e.g. a thin molded packaging material which may be formed into two parts, an upper part 75 and a lower part 76, which are joined along a flange 78. The lower lip of the flange advantageously comprises a light adhesive coating to facilitate handling and placement of the filter element on support plate 34. Casing 77 of FIG. 6 shows an upper part formed of a printed and generally opaque film 80 and a lower part formed of a thin opaque, vacuum molded material 82.

FIG. 7 shows one section of opaque film 80 to be free of printing or other opaquifying matter and, consequently, forming a transparent window 84 bridging the radial path between the shorter side or oblong area 28 and the outer perimeter of the filter. This window 84 allows an operator to monitor the build-up of waste residue in the filter and to replace the filter after an optimum number of runs. Of course the entire area of the plastic film can be transparent, or opaque, if it is so desired.

The perimeter of the filter means forming oblong area 28 about the slide is uncovered and forms means to permit excess specimen flung off the slide to enter the filter medium. Once inside, the centrifugal force tends to push the excess material back into the filter, i.e. towards the outer wall 86.

Figure 8:
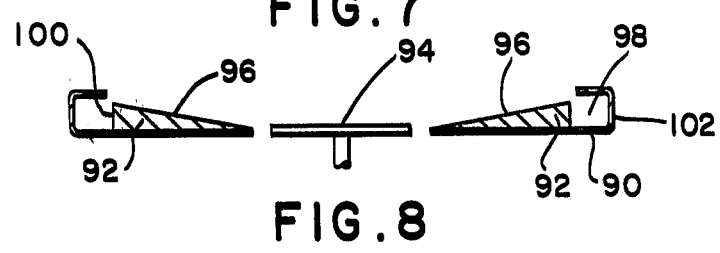
FIG. 8 is a schematic section of an alternative means for collecting wasted blood.

Referring to FIG. 8, another embodiment is seen whereby collecting means 90 comprises a circular ramp member 92 which is mounted, stationary or rotatably, about slide-holder 94 and forms means to intercept waste blood on surface 96 and hold it in a pocket 98 formed by a rear wall 100 of member 92 and outer wall 102 of collecting means 90.

Figure 9:
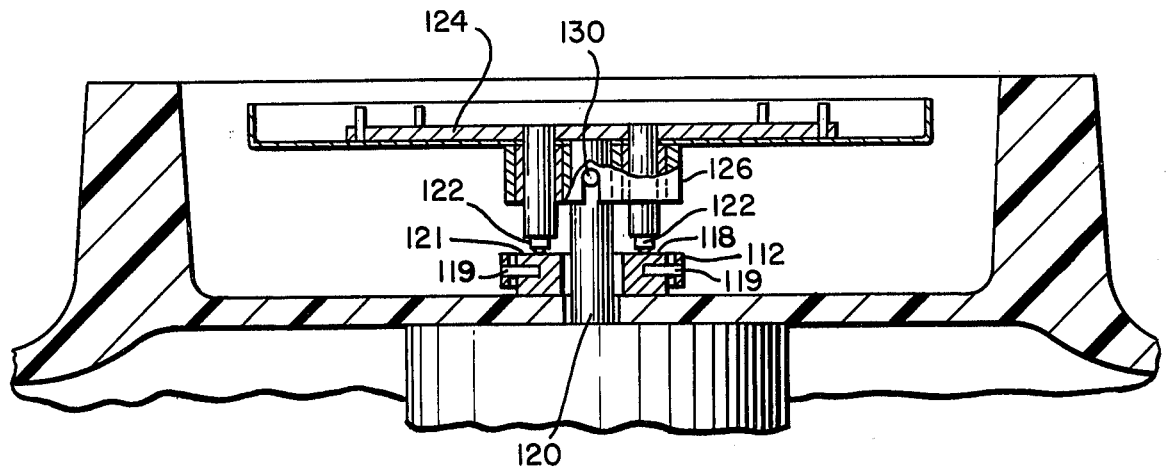
FIGS. 9 and 10 are elevations in section and illustrate an optional embodiment of the invention whereby the slide-supporting member, rather than the waste-blood receiving member, is raised by the opening of the turret cover.
Figure 10:
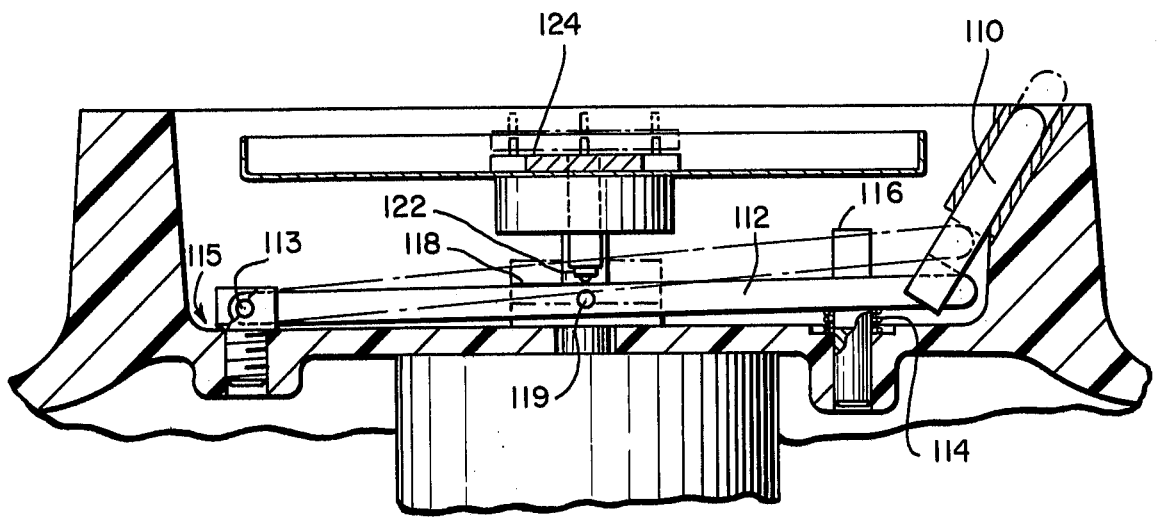

FIGS. 9 and 10 illustrate a still further embodiment of the invention wherein opening of the cover results in raising the slide rather than lowering the waste-blood receiving member. In this embodiment of the invention, a cover 36 (such as seen in FIG. 2) will, on being closed, cause push rod 110 to be depressed, thereby swinging clevis 112 downwardly about a pivot pin 113 which is firmly mounted in the housing at 115. Clevis 112 is biased by a spring 114 mounted about a guidepost 116 containing a slot in which the clevis can move up and down. (Guidepost 116 is shown broken away in FIG. 10 so that the slot is not visible as such but the position of the clevis within the slot is shown.)

When clevis 112 is depressed, it carries with it a ring member 118 which is connected to the clevis member by pins 119. Thus, ring member 118 is adapted for vertical motion along center post 120. Ring member 118, in turn, forms a bearing suface 121 for engaging and lifting or lowering legs 122 which depend directly from a slide-support member 124. The legs are slideably mounted within rotor member 126. Rotor member 126 is locked to the motor driven center post by pin 130. Thus, member 124 is always raised into an upward position when the cover of the apparatus is open and always depressed automatically when the cover is closed.

It is to be understood that the following claims are intended to cover all of the generic and specific features of the invention herein described and all statements of the scope of the invention which might be said to fall therebetween.

What is claimed is:

1. In a centrifuge apparatus, comprising a sample support member, adapted to receive a liquid sample on a sample-receiving surface and to achieve the distribution of said liquid sample as a film over said sample-receiving surface, as said sample-receiving surface is rotated in the plane of said surface the improvement wherein said apparatus comprises waste-receiving and retaining means positioned about the periphery of a sample support member and adapted to receive and hold excess liquid from a plurality of said liquid samples spun off the sample-receiving surface as it rotates, and means to rotate said waste receiving means and said sample support member at substantially the same rpm;

and wherein said waste-receiving and retaining means also forms means to protect other internal surfaces of the apparatus from any contamination with said waste blood and wherein said waste-receiving and retaining means further forms a barrier means to avoid reverse flow of waste blood therefrom.

2. Apparatus as defined in claim 1 wherein said sample-receiving surface and said waste-receiving and retaining means are mounted on two different support means and wherein elevator means are provided to raise and lower said support means for said sample-receiving surface relative to said support means for said waste-receiving and retaining means, said elevator means forming means to facilitate inspection and handling of sample-receiving surface.

3. In a centrifuge apparatus, comprising a sample support member, adapted to receive a liquid sample on a sample-receiving surface and to achieve the distribution of said liquid sample as a film over said sample-receiving surface, as said sample-receiving surface is rotated in the plane of said surface the improvement wherein said apparatus comprises (a) a waste-receiving and retaining means positioned about the periphery of a sample support member and adapted to receive and hold excess liquid from a series of said liquid samples spun off the sample-receiving surface as it rotates and means to rotate said waste-receiving means and said sample support member at substantially the same rpm and wherein said waste-receiving means is formed of a porous medium.

4. Apparatus as defined in claim 3 wherein said sample-receiving surface and said waste-receiving means are mounted on two different support means and wherein elevator means are provided to raise and lower said support means for said waste-receiving means relative to said support for said sample-receiving surface, said elevator means forming means to facilitate inspection and handling of said sample-receiving surface.

5. Apparatus as defined in claim 4 comprising a biasing means and a pivtoally mounted cover of a housing enclosing all said support means, said biasing means forming means to move one of said waste receiving means and said support means vertically when said cover is pivoted to an open or shut position.

6. Apparatus as defined in claim 5 wherein said waste-receiving means is positioned within 0.5 inches of said sample-receiving surface.

7. Apparatus as defined in claim 4 wherein said waste-receiving means is positioned within 0.5 inches of said sample-receiving surface.

8. Apparatus as defined in claim 3 wherein said waste-receiving means is positioned within 0.5 inches of said sample-receiving surface.

9. Apparatus as defined in claim 3 wherein said porous medium is in the form of a porous pad having a central opening therein to position said sample-receiving surface in approximately the same plane as said porous pad, and wherein said porous pad is enclosed within a liquid-impermeable jacket except for an inner-wall portion facing said sample-receiving surface, whereby said pad can be inserted and removed from said apparatus without contact with an operator's hands.

10. Apparatus as defined in claim 9 wherein said sample-receiving surface and said porous pad are mounted on two different support means and wherein elevator means are provided to raise and lower said waste-receiving means relative to said support means for said sample-receiving surface, said elevator means forming means to facilitate inspection and removal of said sample-receiving surface.

11. Apparatus as defined in claim 10 comprising a biasing means and a pivotally mounted cover of a housing enclosing said support means, said biasing means forming means to move at least one said support means vertically when said cover is pivoted to an open or shut position.

12. Apparatus as defined in claim 9 wherein said liquid-impermeable jacket comprises, along all or at least a portion of the top thereof, a transparent portion forming means to make visible contamination of said pad as it builds up during use of said filter.

13. Apparatus as defined in claim 9 wherein porous pad and said sample-receiving surface are positioned within 0.5 inches one from the other.

14. Apparatus as defined in claim 9 wherein said porous pad is impregnated with a disinfectant which is adapted for activation by said liquid.

15. Apparatus as defined in claim 3 wherein said sample-receiving surface and said porous medium are mounted on two different support means and wherein elevator means are provided to raise and lower said support means for said porous medium relative to said support means for said sample-receiving surface, said elevator means forming means to facilitate inspection and removal of said sample-receiving surface.

16. Apparatus as defined in claim 15 comprising a biasing means and a pivotally mounted cover of a housing enclosing said support means, said biasing means forming means to move at least one said support means vertically when said cover is pivoted to an open or shut position.

17. Apparatus as defined in claim 15 comprising a biasing means and a pivotally mounted cover of a housing enclosing said support means, said biasing means forming means to move at least one said support means vertically when said cover is pivoted to an open or shut position.

* * * * *